US008257315B2

(12) United States Patent
Franer et al.

(10) Patent No.: US 8,257,315 B2
(45) Date of Patent: *Sep. 4, 2012

(54) TROCAR SEAL WITH RETRACTION INDUCED HINGE

(75) Inventors: Paul T. Franer, Cincinnati, OH (US); Thomas A. Gilker, Cincinnati, OH (US); Mark Tsonton, Cincinnati, OH (US); David K Norvell, Monroe, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/901,862

(22) Filed: Oct. 11, 2010

(65) Prior Publication Data

US 2012/0089094 A1    Apr. 12, 2012

Related U.S. Application Data

(63) Continuation of application No. 11/548,469, filed on Oct. 11, 2006, now Pat. No. 7,833,199.

(51) Int. Cl.
*A61M 5/178* (2006.01)

(52) U.S. Cl. .......... 604/167.03; 604/167.06; 604/167.01

(58) Field of Classification Search . 604/167.01–167.06
See application file for complete search history.

(56) References Cited

U.S. PATENT DOCUMENTS

| 5,584,850 | A | | 12/1996 | Hart et al. |
| 5,720,730 | A | * | 2/1998 | Blake, III ................. 604/167.02 |
| 5,895,377 | A | * | 4/1999 | Smith et al. ................... 604/256 |
| 6,123,689 | A | | 9/2000 | To et al. |
| 7,083,626 | B2 | * | 8/2006 | Hart et al. ....................... 606/108 |
| 7,833,199 | B2 | * | 11/2010 | Franer et al. ............. 604/167.03 |
| 2004/0171990 | A1 | * | 9/2004 | Dennis et al. ............ 604/167.03 |
| 2005/0030293 | A1 | | 2/2005 | Lai |
| 2006/0016747 | A1 | | 1/2006 | Sakaino et al. |
| 2007/0255218 | A1 | * | 11/2007 | Franer ...................... 604/167.02 |
| 2008/0171987 | A1 | * | 7/2008 | Franer et al. ............. 604/167.03 |
| 2009/0270813 | A1 | * | 10/2009 | Moreno et al. ........... 604/167.01 |
| 2010/0241083 | A1 | * | 9/2010 | Fisher et al. ............. 604/167.04 |
| 2010/0274193 | A1 | * | 10/2010 | Patton et al. ............. 604/167.01 |
| 2010/0292646 | A1 | * | 11/2010 | Nardeo et al. ........... 604/164.05 |
| 2011/0087169 | A1 | * | 4/2011 | Parihar et al. ............ 604/167.03 |
| 2011/0087170 | A1 | * | 4/2011 | Insignares ................ 604/167.03 |

FOREIGN PATENT DOCUMENTS

| CN | 1394554 | 2/2003 |
| WO | WO 2005/030293 A2 | 4/2005 |
| WO | WO 2006/118650 A1 | 11/2006 |

OTHER PUBLICATIONS

International Search Report dated Apr. 21, 2008; International Application No. PCT/US2007/080390.

* cited by examiner

*Primary Examiner* — Victoria P Shumate

(57) ABSTRACT

A trocar comprising an alignment channel and an instrument seal comprising a bending portion and a base portion. The bending and base portions of the instrument seal are spaced relative the alignment channel such that when a surgical instrument is retracted the bending portion inverts and the lip does not enter the alignment channel.

11 Claims, 6 Drawing Sheets

TROCAR SEAL WITH RETRACTION INDUCED HINGE

RELATED APPLICATIONS

This is a continuation of application Ser. No. 11/548,469, filed Oct. 11, 2006, now U.S. Pat. No. 7,833,199.

BACKGROUND

The use of endoscopic procedures in surgery has become widely accepted. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring.

Numerous endoscopic instruments have been developed that allow the surgeon to perform complex surgical procedures with minimal incisions into the skin and tissue surrounding a particular body cavity or anatomical region. In order to introduce the endoscopic instrumentation into the body cavity, a device known as a "trocar" is often used to puncture and/or cannulate the wall of the body cavity. Trocars are widely known in the art and typically comprise an obturator and a cannula. The obturator typically includes a sharply pointed or appropriately structured tip that facilitates penetration of the body cavity wall. The cannula provides a channel or opening through the body cavity wall through which endoscopic instruments may be introduced and removed by the surgeon.

Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. It is common for a sealing arrangement or seal assembly to be used in association with the trocar to maintain pneumoperitoneum. The seals will generally prevent the insufflatory fluid from escaping while an endoscopic instrument is positioned in the trocar cannula.

No one has previously made or used a trocar or seal in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

DETAILED DESCRIPTION

Figure 1:
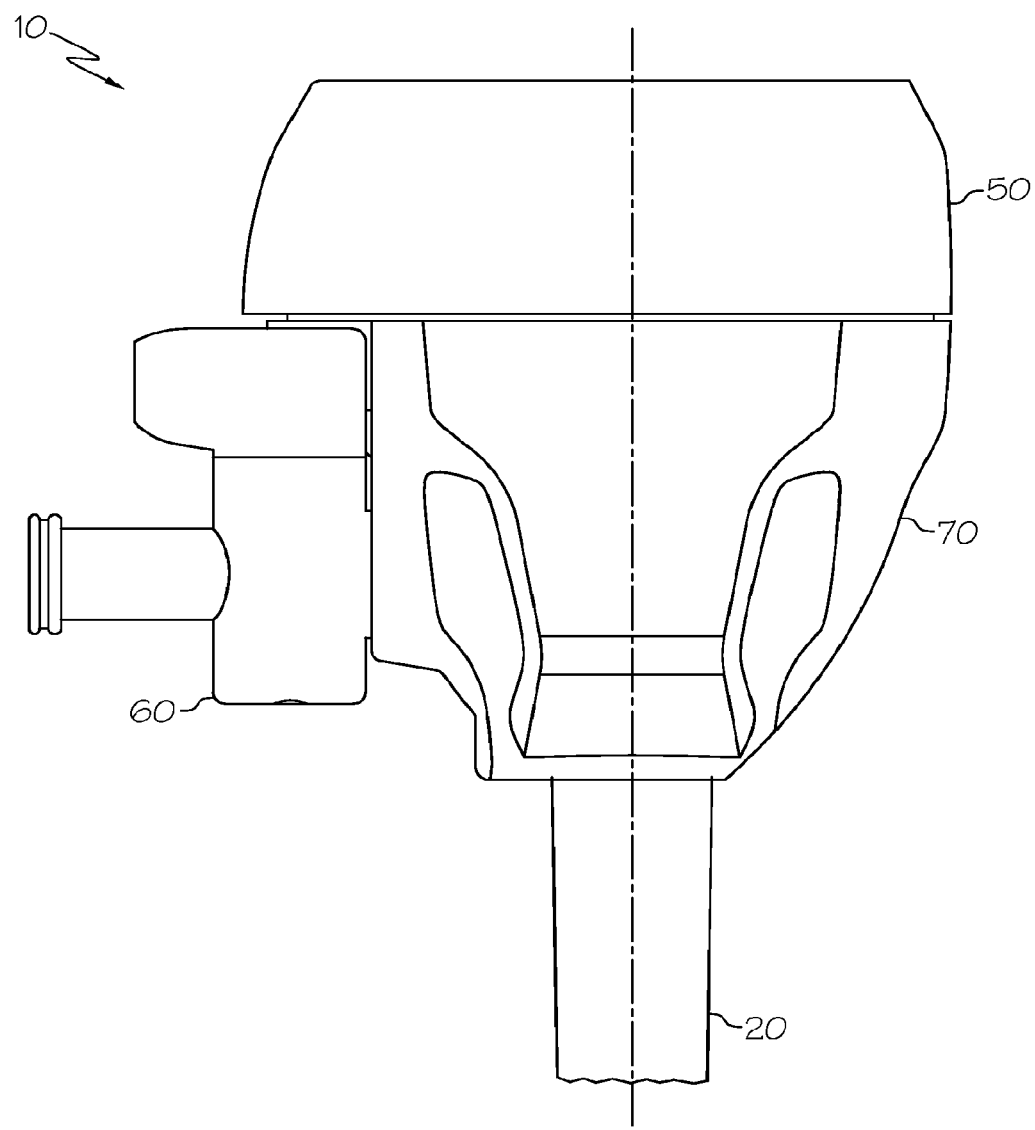
FIG. 1 depicts a plan view of a trocar.
Figure 2:
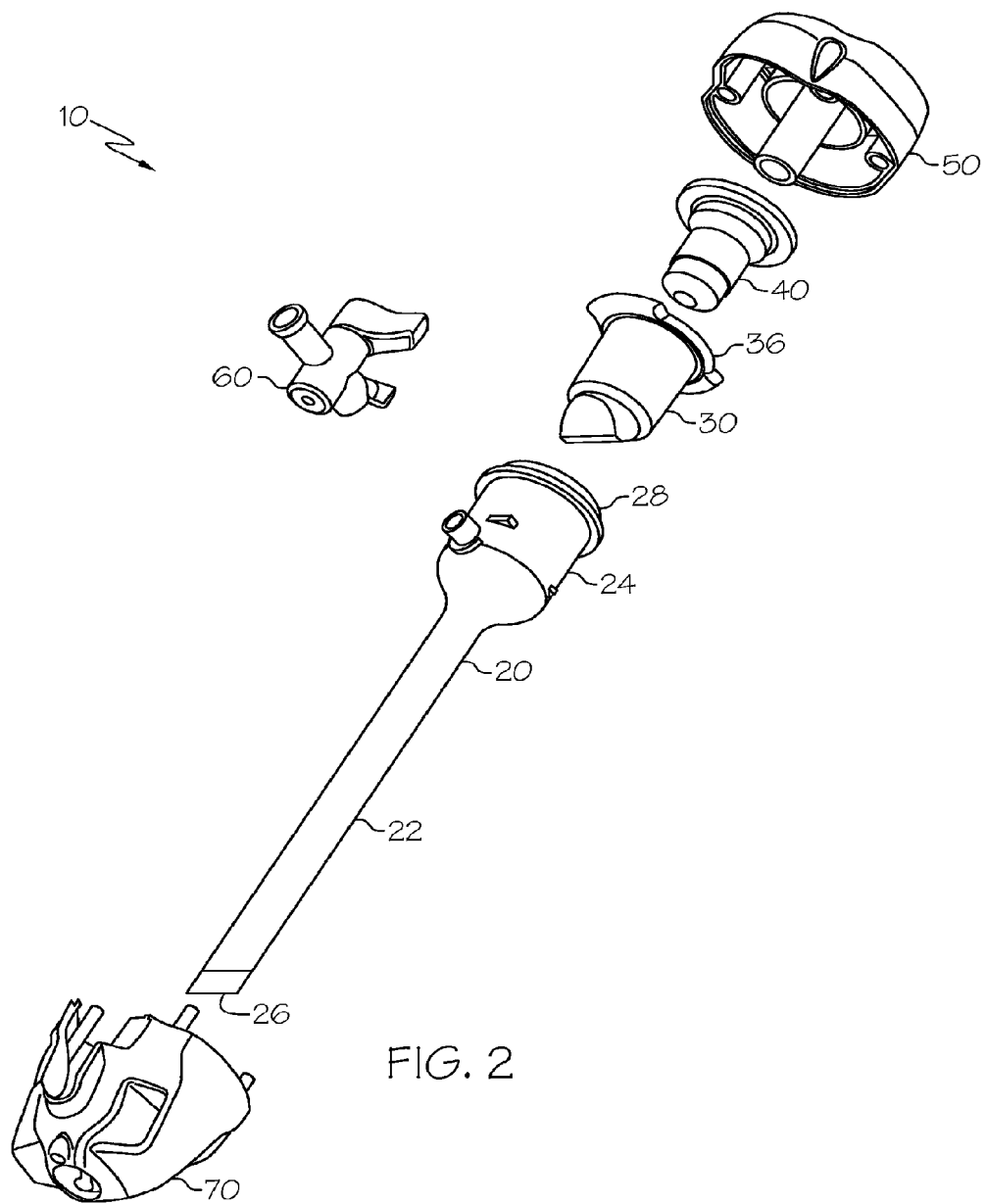
FIG. 2 depicts an exploded view of the trocar of FIG. 1.
Figure 3:
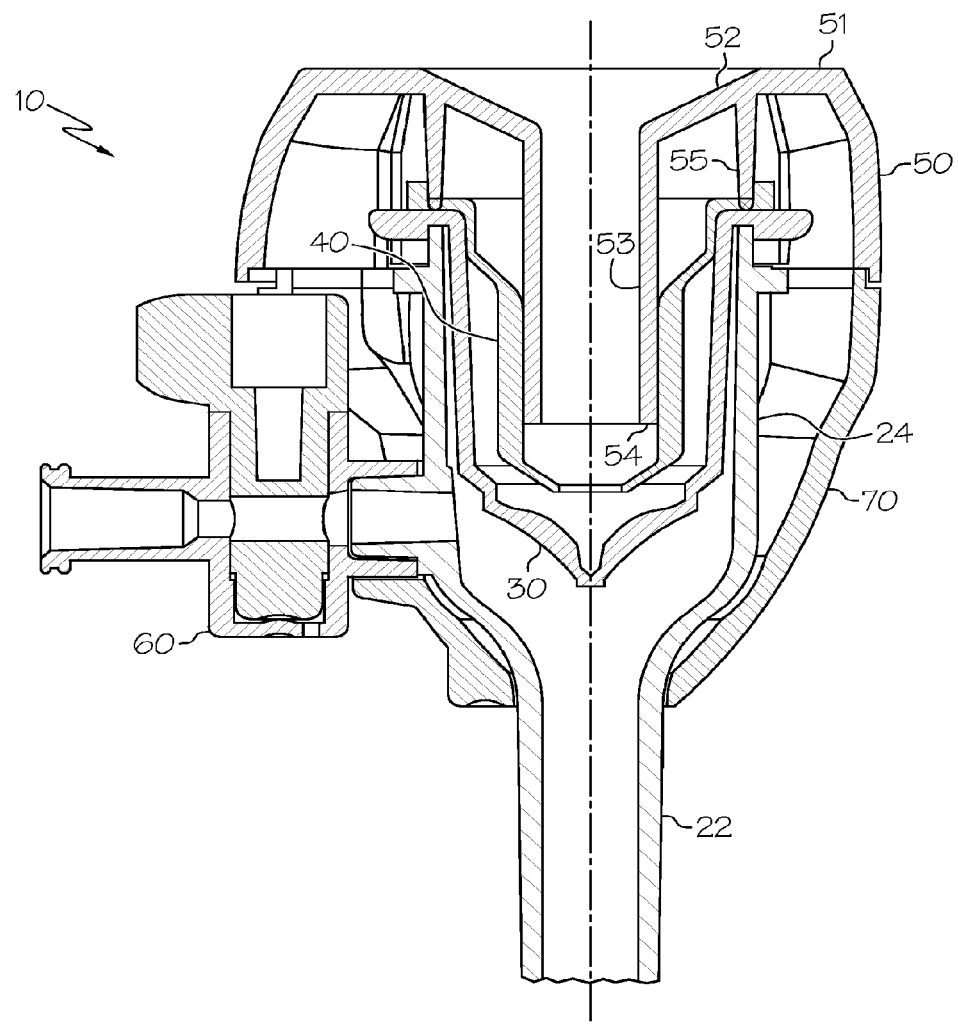
FIG. 3 depicts a cross-sectional view of the trocar of FIG. 1.
Figure 4:
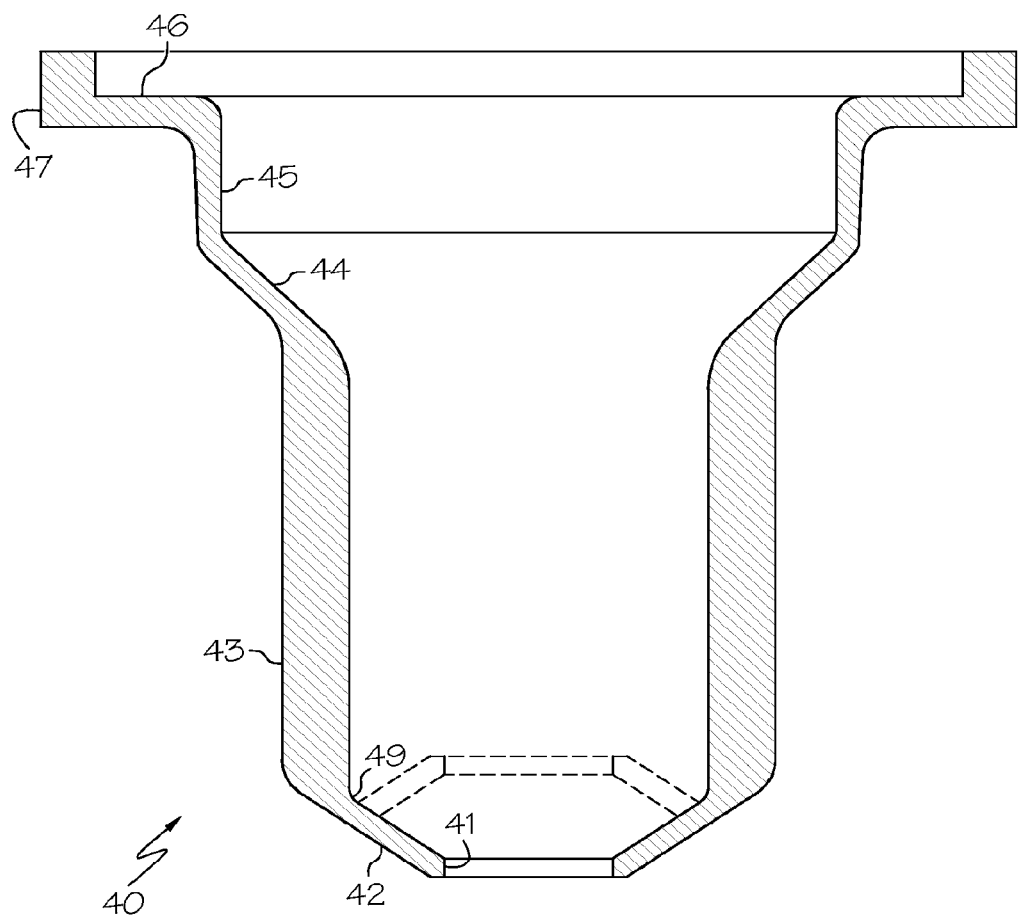
FIG. 4 depicts a cross-sectional view of the instrument seal in FIGS. 2 and 3.

FIGS. 1-4 depict an embodiment of a trocar (10) comprises a tube (20), a top housing (50), and bottom housing (70). A valve (60), shown here as a stopcock, permits the surgeon to selectively introduce or relieve pressurized insufflation fluid through the trocar (10) to the body cavity. Optionally, the trocar (10) may include an obturator (not shown).

The tube (20) includes a cannula (22) and a flared portion (24). The tube (20) provides a passageway for surgical instruments and allows fluid communication between the distal end (26) and the seal seat (28). During typical use the distal end (26) will be inserted through the patient's body wall into the cavity and the seal seat (28) will be positioned outside the patient. The size of the cannula (22) can vary widely, but in the present example the inside diameter is about 5.9 mm.

A seal arrangement comprises a closure valve (30) and an instrument seal (40) that work together to maintain pneumoperitoneum. The closure valve (30) is aligned with and positioned distally relative to the instrument seal (40). In this example, the closure valve (30) is a single-slited "duck bill" valve; however, other types of closure valves may also be used, including flapper valves, multi-slited duck bill valves, and the like. When an endoscopic instrument is passed though the closure valve (30), the valve will open but will generally not provide a complete seal against the instrument. When the instrument is removed the closure valve (30) closes and substantially prevents insufflation fluid from escaping through the trocar (10). The instrument seal (40) seals against the instrument to prevent insufflation fluid from escaping through the trocar (10); however, the instrument seal (40) generally will not maintain pneumoperitoneum unless an instrument is positioned in the trocar (10). As one with ordinary skill in the art will readily recognize, the closure valve (30) and instrument seal (40) can be made from anyone of a variety of flexible and resilient materials such as rubber, polyisopreme, silicone, polyurethane, and the like.

A top housing (50) connects with a bottom housing (70) and holds the assembled trocar (10) together. The top housing (50) includes a proximal end (51) and an alignment channel (53) dimensioned to receive instruments. A tapered transition portion (52) facilitates surgeons inserting instruments into the alignment channel (53). The alignment channel facilitates axial alignment of instruments relative the instrument seal (40) and the cannula (22). In the present embodiment, the alignment channel (53) is rigid and generally cylindrical and is integral molded with the top housing (50). In the present example the inside diameter of the alignment channel (53) is about the same diameter as the cannula (22). The length of the alignment channel (53) may be greater than 2 times the inside diameter. The length of the alignment channel (53) may also be less than 5 times the inside diameter. Naturally, the length to diameter ratios may be outside this range. In the present embodiment, the length is about 3.5 times the diameter.

A shoulder (55) extends distally from the top housing (50) in alignment with the seal seat (28). The shoulder (55) and flared portion (24) house the seal arrangement and alignment channel. The annular mounting seals (36, 46) of the closure valve (30) and instrument seal (40) engage one another and are sandwiched between the shoulder (55) and seal seat (28) to provide a seal at that location.

The instrument seal (40) includes a lip (41) defining an opening aligned with the alignment channel. The lip (41) has an interference fit against instruments inserted into the trocar (10) to provide a seal against the instrument. A bending portion (42) extends laterally and proximally from the lip (41). A base portion (43) extends proximally from the bending portion (42) and abuts the alignment channel (53). In the present embodiment, the bending portion (42) has a generally frustoconical geometry and the base portion (43) has a generally cylindrical geometry. In this embodiment, the bending portion (42) has a thin wall thickness compared the base portion (43), which has a thicker wall thickness. The wall thickness ratio may be between 1.5:1 and 4:1, however, other ratios may also be used. In this embodiment the bending portion is about 0.022" in thickness and the base portion (43) is about 0.06" in thickness. Transition portions (44, 45) extend proximally from the base portion (43) and transition into the mounting seal (46). The transition portion (45) engages the closure valve (30). An proximally extending brim (47) facilitates alignment of the parts during assembly and increases the toughness of the edge to prevent damage to the mounting seal (46) during manufacturing and assembly.

When an instrument is extracted from the trocar (10), the friction with the lip (41) tend to deflect the lip (41) proximally and may cause the bending portion (42) to invert, one example being illustrated in phantom. The deflection induces the bending portion (42) to deflect relative the base portion (43), such as pivoting or bending about the hinge area (49) located adjacent the junction of the bending and base portions (42, 43). The base portion (43) remains relatively stationary when the bending portion (42) inverts. "Relatively stationary" indicates that the base portion (43) has small or no deflection compared to the deflection of the bending portion (42). Thus, even if the base portion (43) may experience a minor deflection, it will nevertheless remain relatively stationary when the bending portion (42) inverts. The distal end (54) of the alignment channel is spaced relative the hinge area (49) and the bending portion (42) such that the lip (41) will be prevented from entering the alignment channel (53) if the bending portion (42) inverts. One benefit of this feature is to prevent binding of the instrument in the alignment channel (53). If the lip (41) would enter the alignment channel (53), the instrument could bind thus increasing the forces needed to extract the instrument.

In the present embodiment, multiple components are in a nested arrangement such that the components are positioned inside one another. The alignment channel (54), instrument seal (40), closure valve (30), flared portion (24), and bottom housing (70) are all nested. In addition to being nested, the majority of the axial length of the alignment channel (54) is axially coincident with the instrument seal (40), the majority of the axial length of the instrument seal (40) is axially coincident with the closure valve (30), the majority of the axial length of the closure valve (30) is axially coincident with the flared portion (24), and the majority of the axial length of the flared portion (24) is axially coincident with the bottom housing (70). Furthermore, the majority of the axial lengths of the alignment channel (54), instrument seal (40), closure valve (30), and flared portion (24) are axially coincident one another.

Figure 5:
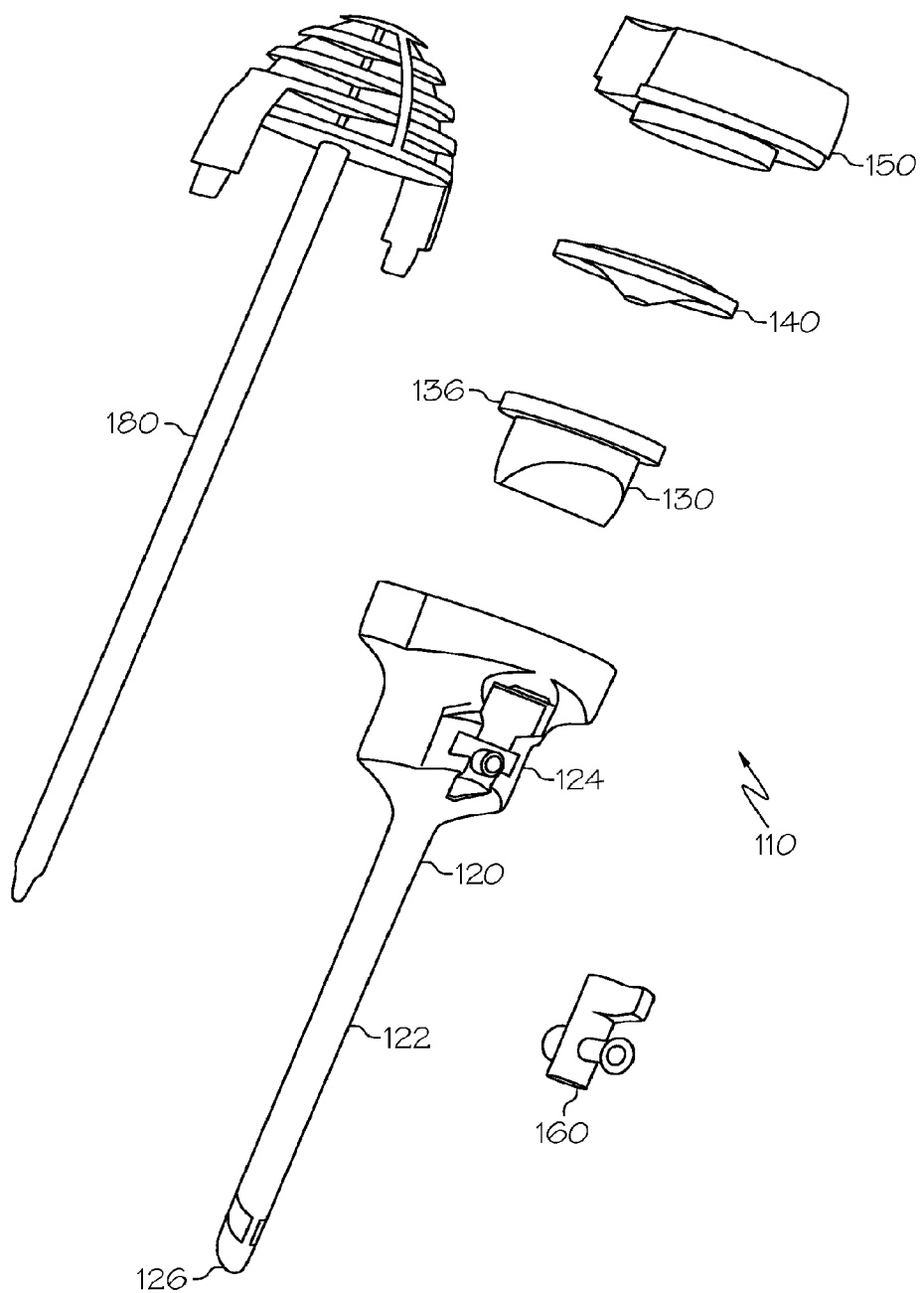
FIG. 5 depicts an exploded view of a trocar.
Figure 6:
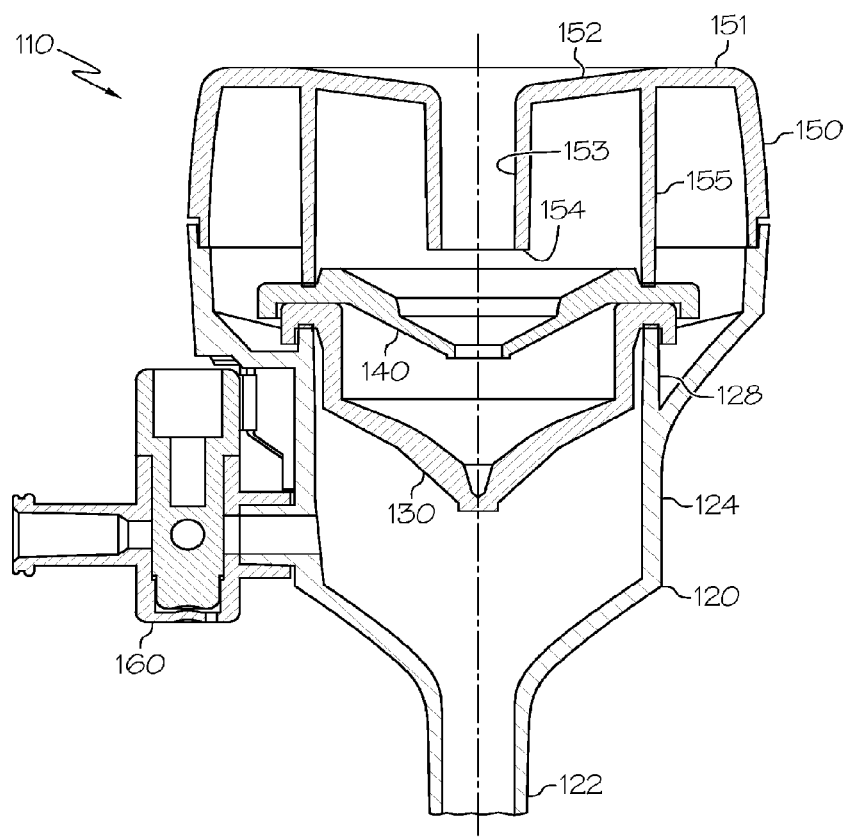
FIG. 6 depicts a cross-sectional view of the trocar of FIG. 5.
Figure 7:
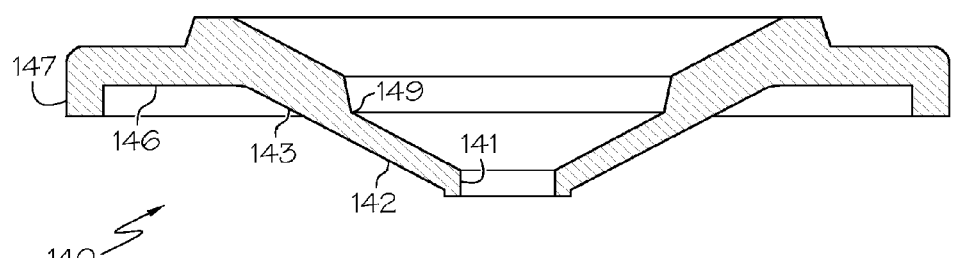
FIG. 7 depicts a cross-sectional view of the instrument seal in FIG. 5.

FIGS. 5-7 depict another embodiment of a trocar (110) comprises a tube (120) and a top housing (150). A valve (160), shown here as a stopcock, permits the surgeon to selectively introduce or relieve pressurized insufflation fluid through the trocar (110) to the body cavity. Optionally, the trocar (110) may include an obtruator (180). The tube (120) includes a cannula (122) and a flared portion (124). The tube (120) provides a passageway for surgical instruments and allows fluid communication between the distal end (126) and the seal seat (128). A seal arrangement comprises a closure valve (130) and an instrument seal (140) that work together to maintain pneumoperitoneum. The closure valve (30) is aligned with and positioned distally relative to the instrument seal (40).

A top housing (150) connects the flared portion (124) and holds the assembled trocar (110) together. The top housing (150) includes a proximal end (151) and an alignment channel (153) dimensioned to receive instruments. A tapered transition portion (152) facilitates surgeons inserting instruments into the alignment channel (153). The alignment channel facilitates axial alignment of instruments relative the instrument seal (140) and the cannula (122). In the present embodiment, the alignment channel (53) is rigid and substantially cylindrical and is integral molded with the top housing (150). In the present example the inside diameter of the alignment channel (153) is about the same diameter as the cannula (122). In the present embodiment, the length of the alignment channel (153) is greater than 2 times the inside diameter.

A shoulder (155) extends distally from the top housing (150) in alignment with the seal seat (128). The shoulder (155) and flared portion (124) house the seal arrangement and alignment channel. The annular mounting seals (136, 146) of the closure valve (130) and instrument seal (140) engage one another and are sandwiched between the shoulder (155) and seal seat (128) to provide a seal at that location.

The instrument seal (140) includes a lip (141) defining an opening aligned with the alignment channel. The lip (141) has an interference fit against instruments inserted into the trocar (110) to provide a seal against the instrument. A bending portion (142) extends laterally and proximally from the lip (141). A base portion (143) is aligned with the bending portion (142) and extends laterally and proximally from the bending portion (142). In the present embodiment, the bending portion (142) has a generally frusto-conical geometry and the base portion (143) also has a generally frusto-conical geometry. In this embodiment, the bending portion (142) has a thin wall thickness compared the base portion (143), which has a thicker wall thickness. The wall thickness ratio may be between 2:1 and 3:1, however, other ratios may also be used. In this embodiment the bending portion (142) is about 0.045" in thickness and the base portion (143) is about 0.095" in thickness. The mounting seal (46) extends laterally from the base portion (143). A distally extending brim (147) facilitates alignment of the parts during assembly and increases the toughness of the edge to prevent damage to the mounting seal (146) during manufacturing and assembly.

When an instrument is extracted from the trocar (110), the friction with the lip (141) tend to deflect the lip (141) proximally and may cause the bending portion to invert. The defection induces the bending portion (142) to deflect relative the base portion (143), such as pivoting or bending about the hinge area (149). The base portion (143) remains relatively stationary when the bending portion (142) inverts. The distal end (154) of the alignment is spaced relative the hinge area (149) and the bending portion (142) such that the lip (141) will be prevented from entering the alignment channel (153) if the bending portion (142) inverts. One benefit of this feature is to prevent binding of the instrument in the alignment channel (153). If the lip (141) would enter the alignment channel (153), the instrument could bind thus increasing the forces needed to extract the instrument.

In the present embodiment, multiple components are nested. For instance, the instrument seal (140), closure valve (130), and flared portion (124) are all nested. In addition to being nested, the majority of the axial length of the instrument seal (140) is axially coincident with the closure valve (130), the majority of the axial length of the closure valve (130) is axially coincident with flared portion (24).

Preferably, the trocars will be processed before surgery. First, a new or used trocar is obtained and if necessary cleaned. The trocar can then be sterilized. In one sterilization technique, the trocar is placed in a closed and sealed container, such as a plastic or TYVEK bag. The container and trocar are then placed in a field of radiation that can penetrate the container, such as gamma radiation, x-rays, or high-energy electrons. The radiation kills bacteria on the trocar and in the container. The sterilized trocar can then be stored in the sterile container. The sealed container keeps the trocar sterile until it is opened in the medical facility.

Having shown and described various embodiments and examples, further adaptations of the methods and apparatuses described herein can be accomplished by appropriate modifications by one of ordinary skill in the art without departing from the scope of the present invention. Several of such potential modifications have been mentioned, and others will be apparent to those skilled in the art. For instance, the specific dimensions described above and scales depicted in the figures will be understood to be nonlimiting examples. Accordingly, the scope of the present invention should be considered in terms of the following claims and is understood not to be limited to the details of structure, materials, or acts shown and described in the specification and figures.

The invention claimed is:

1. An instrument seal for use in a trocar with an alignment channel, the instrument seal comprising a mounting seal, a base portion extending medially and distally from the mounting seal, and a bending portion extending medially from the base portion, the bending portion and base portion being spaced relative to the alignment channel such that when a surgical instrument is retracted the bending portion inverts and does not enter the alignment channel; wherein the base portion has a thickness greater than a thickness of the bending portion.

2. The instrument seal of claim 1, wherein the base portion and bending portion have respective wall thicknesses with a ratio between about 1.5:1 and about 4:1.

3. The instrument seal of claim 1, wherein the bending portion has a generally frusto-conical geometry.

4. The instrument seal of claim 3, wherein the base portion has a generally cylindrical geometry.

5. The instrument seal of claim 1, wherein the bending portion further comprises a lip defining an opening.

6. The instrument seal of claim 1, further comprising a hinge area adjacent the base and bending portions.

7. The instrument seal of claim 1, wherein the mounting seal is annular.

8. A instrument seal for use in a trocar having a cannula with a distal end, a housing with a proximal end, and an alignment channel aligned with the cannula and positioned distally relative to the housing proximal end, the alignment channel having a length and an inside diameter, the length being greater than the inside diameter, the instrument seal comprising:
a lip defining an opening adapted to be aligned with the alignment channel and positioned distally relative to the alignment channel, a bending portion extending laterally and proximally from the lip, a base portion, a hinge area adjacent the base and bending portions, and a mounting seal positioned laterally from the base portion, wherein the base and bending portions have respective wall thicknesses and the base portion is thicker than the bending portion;
wherein the bending and base portions are adapted to be spaced distally from the alignment channel such that when a surgical instrument is refracted the bending portion inverts and the lip does not enter the alignment channel.

9. The instrument seal of claim 8, wherein the thickness ratio of the base portion and bending portion is between about 2:1 and about 3:1.

10. The instrument seal of claim 8, wherein the base portion is adapted to abut the alignment channel.

11. An instrument seal for use in a trocar having a cannula and an alignment channel aligned with the cannula, the alignment channel having a length and an inside diameter, the length being greater than the inside diameter, the instrument seal comprising an opening adapted to be aligned with the alignment channel and positioned distally relative to the alignment channel, a bending portion extending laterally and proximally from the opening, a base portion connected to the bending portion, the base portion being thicker than the bending portion, and a mounting seal positioned laterally from the base portion.

* * * * *